United States Patent [19]

Charpentier et al.

[11] 3,966,553

[45] June 29, 1976

[54] PROCESS FOR PRODUCING CITRIC ACID BY FERMENTATION

[75] Inventors: Jean-Max Charpentier, Montesson; Georges Glikmans, Meudon-la-Foret; Paul Maldonado, Chatou, all of France

[73] Assignees: Institut Francais du Petrole, des Carburants et Lubrifiants et Entreprise de Recherches et d'Activites Petrolieres Elf, Rueil-Malmaison, France

[22] Filed: Dec. 6, 1973

[21] Appl. No.: 422,568

[30] Foreign Application Priority Data

Dec. 6, 1972 France .......................... 72.43480
Dec. 8, 1972 France .......................... 72.43936

[52] U.S. Cl. .............................. 195/28 R; 195/82; 195/114; 195/115
[51] Int. Cl.² ......................................... C12B 1/00
[58] Field of Search .............. 195/28 R, 29, 30, 47, 195/36 R, 82, 115, 114

[56] References Cited

UNITED STATES PATENTS

| | | | |
|---|---|---|---|
| 2,883,329 | 4/1959 | Vergnaud et al. | 195/115 |
| 3,189,527 | 6/1965 | Lockwood et al. | 195/114 |

FOREIGN PATENTS OR APPLICATIONS

| | | | |
|---|---|---|---|
| 1,204,635 | 9/1970 | United Kingdom | 195/30 |

*Primary Examiner*—A. Louis Monacell
*Assistant Examiner*—R. B. Penland
*Attorney, Agent, or Firm*—Millen, Raptes & White

[57] ABSTRACT

Process for manufacturing citric acid by aerobic culture of yeast strains in a medium containing at least one n-paraffin, comprising adding to the culture medium, after the phase of exponential growth thereof, a nitrogenous heterocyclic organic compound selected from α-picolinic acid, 2,6-dipicolinic acid, quinaldic acid, bi-pyridine, orthophenanthroline, 8-hydroxyquinoline and 5-hydroxyquinoxaline, at a concentration from 0.5 to 10 g/liter, and controlling the pH value of said medium during said growth phase by addition of sodium or potassium carbonate.

10 Claims, No Drawings

PROCESS FOR PRODUCING CITRIC ACID BY FERMENTATION

This invention concerns a process for producing citric acid by fermentation.

Citric acid is known as one of the organic acids which are the most commonly used in the food and pharmaceutical industries in view of its easy assimilation and its low toxicity.

It is known that most of the citric acid manufactured in the world is obtained through fermentation processes.

The microorganisms which are the most commonly used in these processes are Aspergillus Niger strains, which use glucides such as molasses and dextroses as the main carbon source.

However, such processes suffer from a number of drawbacks resulting in particular from the instability of the strains and the very long fermentation periods required.

In addition, serious difficulties appear as a result of the variability of composition of the glucides which are used, which is the general case for the products of agricultural origin.

It has been observed a long time ago that yeasts and various metabolites, particularly citric acid, may be produced by fermentation of hydrocarbons, such processes being a priori more advantageous that the processes making use of substrates of agricultural origin (see for example F. JUST, W. SCHNABEL and S. ULMAN, Die Brauerei, Wissenschaftliche Beilage, 1951, 4 (8), 57–60 and (9) 71–75.

It is an object of the present invention to provide an improved process for producing citric acid by using a yeast capable of assimilating normal paraffins, in which said yeast is cultivated in a medium comprising at least one normal paraffin and one aqueous nutrient phase of conventional composition.

As examples of yeasts, we will mention the Endomycetaceae, particularly the Saccharomycetoideae, for example the Pichia, Hansenula, Debaryomyces species, and the Lipomycetoideae, for example of the Lipomyce type. We also have to mention to Cryptococcacae, for example Torulopsis and Candida, and the Rhodotoruloideae, for example Rhodotorula.

According to a first method, the object of the invention consists of producing citric acid by aerobic culture of yeast strains in a medium containing at least one n-paraffin and an aqueous nutrient phase, the method being characterized in that at least one nitrogenous organic heterocyclic compound is added to the medium.

We have now discovered that the yeast strains acquire an increased capacity of accumulating citric acid when adding to the fermentation media organic compounds having at least one amino group included in a ring, i.e. nitrogenous heterocyclic organic compounds. Among these compounds, we prefer, as being more particularly efficient, those which contain at least one carboxylic group in $\alpha$ position of the nitrogen atom of the heterocycle, such as:

2-pyridine carboxylic acid (picolinic acid)
2,6-pyridine dicarboxylic acid (2,6-dipicolinic acid)
quinaldic acid.

These acids may be used in the form of their non-toxic salts, for example their alkali metal salts.

However, other heterocyclic nitrogenous compounds can be used with success.

This is the case of
orthophenantroline
bi-pyridyle
5-hydroxy quinoxaline
8-hydroxy quinoline The process of the invention may be carried out for example by preparing an inoculum of a yeast culture capable of assimilating the n-paraffins, for example Candida, and subsequently performing the fermentation in the presence of at least one paraffin from $C_{10}$ to $C_{24}$.

The inoculum may be prepared by suspending yeast cells, preferably Candida, in aerobic conditions, in an aqueous medium containing an assimilable carbon source, generally an industrial n-paraffinic hydrocarbon cut of from $C_{10}$ to $C_{24}$, and a source of assimilable nitrogen.

The nitrogenous heterocyclic compounds may be added to the inoculum or may be introduced subsequently.

The medium is stirred at a temperature of 25°–30°C for e.g. 36 hours.

After having obtained a sufficient proportion of cells of Candida or another yeast in the inoculum culture, at least a portion thereof is added to the fermentation medium which contains a n-paraffinic carbon source, a source of assimilable nitrogen, as well as different cations, anions and vitamins known as favoring the growth. The nitrogenous heterocyclic compound used in the process of this invention is added either at the beginning of the fermentation step or preferably when the growth of the yeast has been sufficient (end of the exponential phase) or by fractions at each of said stages.

As nitrogen source used in the fermentation medium we may employ, for example, inorganic ammonium salts and preferably ammonium nitrate, ammonium sulfate and ammonium carbonate.

The following cations and anions are also favorable to the growth of the yeasts of the Candida type: potassium, sodium, zinc, magnesium, manganese, iron, phosphate, carbonate.

It is also well known that the addition to the yeast cultures of traces of oligo-elements and vitamins such as thiamine and biotine has a favorable action on the growth of the cells.

After the inoculation, the fermentation takes place in a stirred and strongly ventilated medium at a temperature usually from 25° to 35°C and preferably close to 30°C.

Sterile compressed air is difused through the fermentation medium at a rate of about 1 to 2 liters of air per minute and liter of the medium.

During the first hours of fermentation, i.e. during the growth phase, the pH is preferably so adjusted that the multiplication rate of the yeast cells be optimum, i.e. preferably in the range of from 4.5 to 5.5.

This pH adjustment may be carried out, for example, by addition of a basic aqueous solution such as a solution of ammonia, sodium hydroxide, potassium hydroxide, sodium or potassium carbonate.

However, it is preferred to maintain the pH to the desired value by adding sodium or potassium carbonate in view, not only of the activating effect of the sodium and potassium ions on the growth rate, but also of the effect of the carbonate ions which seem to take part in the metabolism of the yeast cells and activate their growth.

It is after a sufficient growth of the yeasts (end of the growth exponential phase) that we prefer to add the heterocyclic nitogenous organic compounds at a concentration usually from 0.05 to 10 g/liter and preferably from 0.1 to 5 g/liter, and the fermentation continues without the necessity of a pH adjustment by addition of a basic solution, since the pH progressively decreases down to a value of about 3–3.5 at the end of the fermentation stage.

When sufficient amounts of citric acid have been accumulated, this compound may be separated by conventional methods, for example in the form of a calcium salt. After removal of the cells we may, for example, make the medium basic, by addition of the stoichiometrical amount of lime, and thereafter precipitate the calcium citrate by heating the supernatant phase.

According to a second method, the object of the invention consists of producing citric acid continuously in the following manner:

We proceed, in at least one first aerated fermentation zone, to a continuous culture of a yeast capable of assimilating the n-paraffins, in a medium containing permanently all the elements necessary to the growth of said yeast, including at least one n-paraffin, the yeasts are withdrawn at such a rate that they are maintained in the first fermentation zone during their development phase; the withdrawn yeasts are introduced into at least one second aerated fermentation zone containing growth elements but with a low content of assimilable inorganic nitrogen source (particularly ammonium salts); said yeasts are maintained in said second zone for a time sufficient for the excretion of a significant amount of citric acid, said citric acid and the yeasts of the culture medium of said second zone being separated in a known manner. In this process the rate of dilution in the first zone is from 0.05 to 0.3 h$^{-1}$ and in the second zone is preferably from 0.01 to 0.04 h$^{-1}$.

This second method concerns a continuous process for producing metabolites, in the present case citric acid, by fermentation making use of yeasts grown on n-paraffins. An entirely continuous fermentation of yeast has already been developed for the production of proteins and has a number of advantages as compared to a batchwise process but in the case of metabolites production, the difficulties are greater since the excretion occurs in conditions where the growth is limited so that the growth and the excretion are in opposition. Finally, it is worth to mentioning that, in the continuous fermentation processes, inhibition effects frequently occur due to the excreted products and particularly due to the main product. The process of the first abovementioned method may be carried out continuously, but, however, it still suffers from the following few drawbacks: It has been observed that the excretion of citric acid occurs when the rate of growth of the microorganism is small or nil; consequently the only way is to proceed with an excretion at a low rate of growth in order to ensure the development of the micro-organisms. In these working conditions, it has been observed that the production of citric acid per unit by weight of yeasts was less than in a batchwise process and therefore resulted in a decreased yield.

However, we have discovered that when the growing phase is separated from the excretion phase, by means of a multistage culture, a high production of citric acid as well as high yields were obtained. Furthermore it has surprisingly been observed that, in this type of culture, the system is highly stable. This second method thus relates to a process for continuously producing citric acid and has the particular feature of comprising two fermentation steps, the first one being used for the growth of the yeast and the second for the excretion of the citric acid. This process provides for the recovery, either continuously or not, of the formed acid and of the yeasts which may be used as food constituent.

By medium of low inorganic nitrogen content (present in the second fermentation zone), is meant a medium whose inorganic nitrogen content is either insufficient to permit a substantial multiplication of the yeasts or preferably almost nil.

In practice we may feed the first fermentation zone with an amount of inorganic nitrogenous compound, just sufficient for complying with the growth requirements of the yeasts, taking into account the rate of development of the yeast selected for said first zone, so that the inorganic medium passing from the first to the second fermentation zone will only contain an insufficient amount of inorganic nitrogen source for making possible a substantial development of the yeast in said second zone. It is however advantageous to concentrate the yeast before introducing it into the second zone in order to avoid, as much as possible, the passage of the inorganic nitrogenous compound from the first to the second zone.

As indicated above, these results are achieved with a dilution rate D from 0.05 to 0.3 h$^{-1}$ in the first stage, the rate of dilution in the second stage being preferably from 0.01 to 0.04 h$^{-1}$.

It is recalled that the dilution rate in a given fermentation zone is the following ratio:

$$\frac{\text{Rate of introduction (or withdrawal) of the fermentation medium, expressed by volume per hour}}{\text{reactor volume}}$$

It is thus the inverse of a residence time.

This second method for producing citric acid may be carried out in the following manner:

In a first stage, called "starting stage", we introduce a strain of n-paraffins consuming yeast in a first strongly ventilated fermentation vessel, containing a conventional culture medium using a hydrocarbon as carbon source. The conventional culture media are well-known; they are the same as those used in the first method as above-described and generally they contain at least one n-paraffinic hydrocarbon, inorganic salts required for the growth, including in particular a source of inorganic nitrogen and phosphorus, for example ammonium and phosphate salts, and growth elements (vitamins, oligo-elements).

When the desired cell concentration is attained, the culture is made continuous by introducing fresh medium and hydrocarbon and withdrawing the fermentation medium at a rate corresponding to the selected dilution rate. The pH is adjusted to a value from 2.5 to 6 and preferably from 4.5 to 5.5 by adding a base which may be ammonia, an alkali metal carbonate or potassium or sodium hydroxide. Two operating ways are thus possible:

1. The withdrawn medium is directly injected from the first stage to the second stage which contains a culture medium or low nitrogen content.

2. The yeasts are injected in the second stage after separation from the aqueous medium, for example by decantation, so as to concentrate the biomass. This second stage contains the same elements as for the preceding solution.

Whatever the selected procedure, the second reactor has to be fed with a complete culture medium, with the exception of the inorganic nitrogen source i.e. containing in particular inorganic salts with the exception of nitrogenous salts, vitamins, oligoelements and at least one paraffin, so as to ensure the conversion of the hydrocarbons to citric acid with a high yield.

The medium withdrawn from the second stage is then treated in a known manner for recovering citric acid.

Some particular features in the operation of the process according to said second method need to be mentioned:

1. The volume ratio $V_2/V_1$ of the second stage reactor ($V_2$) to the first stage reactor ($V_1$), is usually from 5 to 20; the optimum value being about 10.

2. The dilution rate (D) in the first stage is from 0.05 to 0.30 $h^{-1}$ and preferably from 0.15 to 0.20 $h^{-1}$, since these conditions are those for which the rate of production of citric acid is the highest.

3. The dilution rate in the second stage may be in the range of from 0.01 to 0.04 $h^{-1}$ and is preferably close to 0.02 $h^{-1}$, which corresponds to a residence time in the reactor of about 50 hours; after this time, the activity of the yeast is still constant.

4. The cell proportion (dry weight) in the two stages may vary, for example, from 5 to 40 grams per liter. It is preferably about 20 g/liter since for a lower value the productivity decreases and for a higher value the yield begins to decrease.

5. The temperature is preferably from 25° to 38°C.

6. The feeding rate of n-paraffin to the second fermentation zone is preferably from 0.2 to 2 g/liter/hour.

Another embodiment of this culture system has been experienced for the production of metabolites in semicontinuous culture, particularly in the case of stains having enzymes sensitive to the excretion products.

In fact, it is possible to produce a metabolite (in the present case, citric acid) by cultivating in a first stage, operated in a continuous manner, yeasts which will be injected into the various excretion reactors, batchwise operated.

Surprisingly, it has been observed that the system of this second method produces better results than those obtained in a batchwise manner or with a single-stage continuous culture.

This second method has a number of advantages with respect to the processes known up to now. It not only results in very high yields, but also in a much more economical production, since it results in a hourly production gain of about 30 % over the batchwise processes.

Moreover, this second method gives a product whose composition is exactly reproducible from one day to another, which is a great advantage for the treatment and the use.

Finally, the continuous system makes it possible to have a perfect technological and physiological control of the process.

It must be observed, in addition, that this system may be applied to any synthesis of metabolites and particularly of the metabolites produced during the stationary phase, for example α-ketoglutaric acid, fumaric acid, malic acid and certain amino acids.

An improvement of this second method consists of adding to the second fermentation zone, one of the above-defined organic heterocyclic compounds for carrying out the first method for obtaining citric acid, the heterocyclic organic compound being used at a concentration also defined as hereabove indicated.

The following non-limitative examples relate to preferred embodiments of these two methods of the invention.

It must be understood that in the two above-described methods, there can be used mutants of yeasts, particularly mutants of Candida or variants obtained through physical techniques such as X rays or UV rays, or through chemical techniques, such as the use of nitrosomethylurethane or nitrosoguanidine, well known for their mutagenic action.

EXAMPLE 1 (Comparative example)

We inoculate cells of Candida lipolytica IFP 29 on gelose, into a flask of a 100 ml capacity, containing 20 ml of a preculture liquid medium having the following composition:

| | |
|---|---|
| $KH_2PO_4$ | 3.4 g/liter |
| $Na_2HPO_4$, 12 $H_2O$ | 1.5 g/liter |
| $MgSO_4$, 7 $H_2O$ | 0.7 g/liter |
| $(NH_4)_2SO_4$ | 4 g/liter |
| $CaCl_2$ | 0.1 g/liter |
| $FeSO_4$, 7 $H_2O$ | 2 mg/liter |
| $CuSO_4$, 5 $H_2O$ | 5 μg/liter |
| $H_3BO_3$ | 10 μg/liter |
| $MnSO_4$, $H_2O$ | 10 μg/liter |
| $ZnSO_4$, 7 $H_2O$ | 10 μg/liter |
| $(NH_4)_6M_7O_{24}$, 4 $H_2O$ | 100 μg/liter |
| $Co(NO_3)_2$, 6$H_2O$ | 10 μg/liter |
| Yeast extract | 100 mg/liter |
| Tap water | complement to 1 liter |
| $C_{12}$—$C_{19}$ n-paraffin cut | 15 g/liter |

The n-paraffin cut has the following composition:

| Hydrocarbon | % by weight |
|---|---|
| $C_{12}$ | 0.07 |
| $C_{13}$ | 2.05 |
| $C_{14}$ | 15.71 |
| $C_{15}$ | 32.00 |
| $C_{16}$ | 30.83 |
| $C_{17}$ | 17.90 |
| $C_{18}$ | 1.38 |
| $C_{19}$ | 0.06 |

The Candida cells are incubated at 30°C after the flask containing the inoculum has been secured to a stirring table driven at a speed of 140 r/mn. After incubation for 36 hours, 10 ml of said inoculum are inoculated into a Fernbach flask of 1.5 liter capacity containing 200 ml of sterile nutrious medium A having the following composition:

| | |
|---|---|
| $KH_2PO_4$ | 2 g/liter |
| $MgSO_4$, 7$H_2O$ | 1 g/liter |
| $NH_4NO_3$ | 2.5 g/liter |
| $CaCO_3$ | 20 g/liter |
| $FeSO_4$, 7$H_2O$ | 0.2 g/liter |
| $MnSO_4$, 7$H_2O$ | 0.026 g/liter |
| Yeast extract | 100 mg/liter |
| Tap water | complement to 1 liter |
| $C_{12}$—$C_{19}$ n-paraffin cut | 25 g/liter |

The Fernbach flask is secured onto a stirring table and the medium is stirred for 6 days at 30°C.

The citric acid concentration is 10.1 g/liter.

EXAMPLE 2

The fermentation described in example 1 is repeated after addition of 1.2 g/liter of α-picolinic acid to medium A. The citric acid concentration is 26 g/liter.

EXAMPLE 3

The fermentation described in example 2 is repeated with similar results while using, in lieu of the Candida lipolytica strain IFP 29, anyone of the following strains of yeasts of the Candida type:

| Strains of the Candida type | No. |
|---|---|
| lipolytica | IFP 102 |
| lipolytica | IFP 88 |
| lipolytica | ELF 8 |
| lipolytica | ELF 19 |
| lipolytica | ELF 25 |
| tropicalis | IFP 114 |
| lipolytica diploide | D 1805 |
| lipolytica diploide | D 1806 |
| lipolytica diploide | D 1807 |

EXAMPLE 4 (comparative example)

We sterilize a fermentation vessel of a 2.5 liter capacity, containing 1.2 liter of a nutrious medium having the following composition:

| | |
|---|---|
| $KH_2PO_4$ | 4 g/liter |
| $MgSO_4$, 7 $H_2O$ | 2 g/liter |
| $NH_4NO_3$ | 5 g/liter |
| $FeSO_4$, 7 $H_2O$ | 0.4 g/liter |
| $MnSO_4$, 7 $H_2O$ | 0.052 g/liter |
| Yeast extract | 200 mg/liter |
| Thiamine chlorhydrate | 50 μg/liter |
| Tap water | complement to 1 liter |
| $C_{12}$—$C_{19}$ n-paraffin cut | 100 g/liter |

We inoculate into the fermentation vessel 200 ml of a preculture medium having the composition according to example 1, by using a strain of Candida lipolytica IFP 29.

The pH is adjusted in a first phase at the value of 5 by addition of a solution of potassium carbonate 0.5 M. The medium is then stirred at 2300 r/mn for about 30 hours at a temperature of 30°C. Then the medium is allowed to acidify by itself and it is observed that the pH is stabilized at a value from 3 to 3.5. After 150 hours of culture, the citric acid concentration is 65 g/liter.

EXAMPLE 5

The fermentation described in example 4 is repeated after addition of 1.2 g/liter of α-picolinic acid to the medium, after 30 hours of culture. The citric acid concentration after 150 hours is 135 g/liter.

EXAMPLES 6 – 11

The fermentation described in example 5 is reproduced by using, in lieu of α-picolinic acid, 1.2 g/liter of each of the following nitrogenous heterocycles:
- 2,6-pyridine-dicarboxylic acid
- quinaldic acid
- bi-pyridine
- orthophenanthroline
- 8-hydroxy-quinoline
- 5-hydroxy-quinoxaline When using 2,6-pyridine-dicarboxylic acid and quinaldic acid, we obtain a citric acid concentration of about 130 g/liter after 150 hours. The citric acid concentration after 30 hours is about 115 g/liter when using bi-pyridine, orthophenanthroline, 8-hydroxy-quinoline and 5-hydroxy-quinoxaline,

EXAMPLE 12

The fermentation described in example 4 is repreated after addition of 0.06 g/liter of quinaldic acid to the medium, after 30 hours of culture.

After 150 hours of culture at 30°C and at a pH of 4.5, the citric acid concentration is 85 g/liter.

EXAMPLE 13

The fermentation described in example 4 is repeated after addition of 0.15 g/liter of quinaldic acid to the medium, after 30 hours of culture.

After 150 hours of culture, the citric acid concentration is 117 g/liter.

EXAMPLE 14

This example illustrates the case of a continuous culture in a single stage.

We proceed first to a preculture in a Fernbach flask of the strain of Candida lipolytica IFP 29.

The composition of the medium is as follows (per liter):

| | |
|---|---|
| $KH_2PO_4$ | 2 g |
| $MgSO_4$, 7 $H_2O$ | 1 g |
| $NH_4NO_3$ | 2.5 g |
| $CaCO_3$ | 20 g |
| $FeSO_4$, 7 $H_2O$ | 0.2 g |
| $MnSO_4$, 7 $H_2O$ | 0.026 g |
| Yeast extract | 100 mg |
| Tap water | complement to 1000 ml |
| $C_{12}$—$C_{19}$ n-paraffin cut | 25 g per liter of said medium |

The Fernbach flask is secured onto a stirring table and the medium is stirred for 3 days at 30°C; we use 200 ml of preculture as inoculum for the fermentation vessel.

The fermentation vessel is a reactor having a 2.5 liters capacity and containing 1.3 liter of an aqueous sterile medium A, having the following composition per liter:

| | |
|---|---|
| $KH_2PO_4$ | 4 g |
| $MgSO_4$, 7 $H_2O$ | 2 g |
| $NH_4NO_3$ | 5 g |
| $FeSO_4$, 7 $H_2O$ | 0.4 g |
| $MnSO_4$, 7 $H_2O$ | 0.052 g |
| Yeast extract | 200 mg |
| Thiamine chlorydrate | 50 g |
| Tap water | complement to 1000 ml |

To this medium we add the $C_{12}$–$C_{19}$ cut in such an amount that its concentration is 20 g/liter and the culture is started at pH 5 at 30°C under aeration. After 30 hours of culture we observe a production of about 15 g/liter (dry weight). We select this time for starting the continuous culture by injecting, on the one hand, the medium A further containing 1.2 g/liter of α-picolinic acid, and on the other hand, 1.65 g per liter and per hour of $C_{12}$–$C_{19}$ hydrocarbons. We withdraw an equal volume of the culture medium. The dilution rate is 0.05 $h^{-1}$; the hourly production amounts to 1.02 g/liter of citric acid and 0.98 g/liter of yeast. Accordingly, the citric acid yield is 62 % with respect to the converted hydrocarbon.

With the same procedure but without α-picolinic acid, the citric acid yield by weight is only 32 %.

EXAMPLE 15

In this example, the continuous fermentation described in example 14 is repeated while proceeding with a dilution rate of 0.02 h$^{-1}$ and an hourly hydrocarbon flow rate of 1.04 g/liter.

We obtain a hourly yield of 1.03 g/liter of citric acid and 0.40 g/liter of yeast. The citric acid yield by weight is 99 % with respect to the converted hydrocarbon.

EXAMPLE 16

This example illustrates more particularly the second method of producing citric acid. The preculture is carried out as described in example 14. We inoculate said preculture into a so-called "first stage" reactor having a capacity of 2.5 liters wile proceeding as described at the beginning of example 14. After 30 hours of culture at pH 5 and 30°C, the medium is fed continuously at the moment where the dry weight of the culture amounts to about 15 g/l. The selected dilution rate is 0.1 h$^{-1}$; the hourly flow rate of hydrocarbon is 2 g/liter. The culture medium is withdrawn at a rate substantially equal to the feeding rate. In these conditions the yeast concentration is kept substantially constant. No α-picolinic acid is introduced into the medium of this fermentation vessel. We progressively transfer the yeasts into the second stage, called "excretion stage", whose volume is 25 liters.

This reactor contains a medium whose composition is the same as that of medium A, but without nitrogen source.

At the time of starting the injection of the yeast into the second stage, we inject n-paraffin at an hourly rate of 0.57 g/liter and α-picolinic acid in such an amount that the stationary concentration of said acid be 1.2 g per liter. The pH is autoregulated at 3.2, the temperature is 30°C. We withdraw the medium at a rate substantially equal to the feeding rate. In the fermentation vessel, the cell concentration is stabilized at 19.5 g/liter for a dilution rate of 0.01 h$^{-1}$.

The outflow, continuously withdrawn, contains 99.2 g/l of citric acid. We thus obtain hourly 0.99 g/liter of citric acid and 0.395 g/liter of cells. The citric acid yield in the second stage is consequently 174 %, the total yield 128 % by weight with respect to the consumed hydrocarbon.

When no α-picolinic acid is added in the second stage, the citric acid yield of said second stage is only 78 % with respect to the converted hydrocarbon.

EXAMPLE 17

The conditions are the same as those described in example 16, but in the second stage, the residence time is reduced by continuously adding the medium A without nitrogen step so that the dilution rate is 0.02 h$^{-1}$. In these conditions, the cell concentration on the leaving of the fermentation vessel, is 10.3 g/liter. The outflow contains 49.2 g/liter of citric acid, this corresponding to an hourly production of 0.98 g/liter. The hourly production of yeast is 0.206 g/liter. The total citric acid yield by weight is 124 % with respect to the converted hydrocarbon.

EXAMPLE 18

The conditions are the same as in example 16, but the dilution rate in the first stage is 0.2 h$^{-1}$. When the culture is in equilibrium state, it has a cell concentration of 10.4 g/liter and we inject it into the excretion stage. In these culture conditions the dilution rate in the excretion reactor is 0.02 h$^{-1}$ as in example 17 but the activity of the yeast is higher. As a matter of fact we add in this case 0.80 g/l/h of $C_{12}$–$C_{19}$ cut and from the effluent we recover 71 g/liter of citric acid. The hourly production is accordingly 1.42 g/liter of acid and 0.2 g/l of yeast. The total citric acid yield is 142 %.

EXAMPLE 19

The conditions are the same as in example 16, but the dilution rate in the first stage is 0.08 h$^{-1}$. In these conditions, at the equilibrium, the dry weight is 30.4 g/liter. The effluent from the first stage is then introduced into the second stage in which we add, as precedingly, α-picolinic acid in such an amount as to obtain a stationary concentration of 1.2 g/liter of said acid and n-paraffins are introduced at a rate of 0.84 g/liter. Simultaneously we add medium A into the excretion stage so that the dilution rate ($D_2$) be 0.01 h$^{-1}$. The cell concentration at the equilibrium in the second stage is 24.5 g/liter.

In these conditions, the citric acid concentration, at equilibrium, is 122 g/liter. The hourly production of said acid is 1.22 g/liter. The total yield of citric acid is 113 %.

EXAMPLE 20

Example 16 is repeated except that a dilution rate of 0.2 h$^{-1}$ is maintained in the first stage. After stabilization of the culture, the withdrawn medium is subjected twice to a cell concentration by means of a decantation system provided for this purpose and is injected into an excretion reactor whose volume is 12.5 liters. We add simultaneously 0.90 gl$^{-1}$ h$^{-1}$ of hydrocarbon and corresponding α-picolinic acid at a stationary concentration of 1.2 g/liter.

In these conditions, the dilution rate ($D_2$) in the second stage is 0.02 h$^{-1}$ and the cell concentration 19.8 g/liter.

The observed citric acid concentraion in the excretion reactor is 82 g/l, which corresponds to a hourly production of 1.64 g/l. The total yield of citric acid is 127 %.

EXAMPLE 21

We repeat example 16 except that we maintain in the first stage a dilution rate ($D_1$) of 0.13 h$^{-1}$. The hourly flow rate of hydrocarbon in said stage is 2.1 g/l. We inject at the equilibrium a dry weight of cells of 16.3 g/l. This medium is injected continuously into the excretion reactor having a volume of 25 liters. After equilibrium of said second stage, operated at $D_2$ = 0.013, and in which we inject 1 g/l/h of hydrocarbon as well as α-picolinic acid (stationary concentration of 1.2 g/l) we measure a dry weight of cells of 16.1 g/l and an acid concentration of 87 g/l. The hourly production is 1.13 g/l. The total citric acid yield is 123 %.

We claim:

1. A process for continuously manufacturing citric acid comprising in at least one first aerated fermentation zone, continuously growing a culture of yeast capable of assimilating n-paraffins, in a medium containing all the elements required for the growth of said yeast, including at least one n-paraffin, continuously withdrawing the yeasts at such a rate that they be kept in the first fermentation zone during their development phase, continuously introducing the withdrawn yeasts into at least one second aerated fermentation zone separate and distinct from the first aerated fermentation zone and containing growth elements, but having a low content of assimilable inorganic nitrogen source, at least one nitrogenous heterocyclic compound at a concentration of from 0.5 to 10 g/l being added to said second fermentation zone, maintaining said yeasts in said second zone for a sufficient time to excrete citric acid and separating the citric acid and the yeasts from the culture medium of said second zone, the dilution rate being from 0.15 to 0.2 $h^{-1}$ in said first fermentation zone, and 0.1 to 0.04 $h^{-1}$ in said second fermentation zone, the cell concentration in both fermentation zones being about 20 g/l.

2. A process according to claim 1, in which the volume of said second zone is from 5 to 20 times the volume of said first zone.

3. A process according to claim 1, in which the pH is maintained between 2.5 and 6 in the first fermentation zone.

4. A process according to claim 1 in which the pH in the second fermentation zone is not controlled and is allowed to change.

5. A process according to claim 1, in which the rate of introduction of n-paraffin into the second fermentation zone is from 0.2 to 2 g/l/h.

6. A process according to claim 1, in which the effluent from the first fermentation zone is treated to remove water therefrom to provide a more concentrated mass of the yeast cells before said yeast cells are introduced into the second fermentation zone.

7. A process according to claim 1 in which the yeast strain is of the Candida type.

8. A process according to claim 1, wherein said nitrogenous heterocyclic compound is α-picolinic acid, 2,6-dipicolinic acid, quinaldic acid, bi-pyridine, orthophenanthroline, 8-hydroxyquinoline or 5-hydroxyquinoxaline.

9. A process according to claim 8, in which the yeast strain is of the Candida type.

10. A process as defined in claim 1, wherein the dilution rate in the second stage is about 0.02 $h^{-1}$.

* * * * *